United States Patent
Zhou

(10) Patent No.: US 9,468,500 B2
(45) Date of Patent: Oct. 18, 2016

(54) IMAGE-GUIDED LASER CATHETER

(75) Inventor: Gan Zhou, Plano, TX (US)

(73) Assignee: TEA TIME PARTNERS, L.P., Rockwall, TX (US)

( * ) Notice: Subject to any disclaimer, the term of this patent is extended or adjusted under 35 U.S.C. 154(b) by 2387 days.

(21) Appl. No.: 11/315,546

(22) Filed: Dec. 22, 2005

(65) Prior Publication Data
US 2006/0241572 A1  Oct. 26, 2006

Related U.S. Application Data

(60) Provisional application No. 60/675,046, filed on Apr. 26, 2005.

(51) Int. Cl.
| | |
|---|---|
| *A61B 18/20* | (2006.01) |
| *A61B 18/24* | (2006.01) |
| *A61B 8/12* | (2006.01) |
| *A61B 8/00* | (2006.01) |
| *G01S 15/89* | (2006.01) |
| *G10K 15/04* | (2006.01) |
| *A61B 18/26* | (2006.01) |

(52) U.S. Cl.
CPC ................ *A61B 18/24* (2013.01); *A61B 8/12* (2013.01); *A61B 8/4483* (2013.01); *G01S 15/8965* (2013.01); *G10K 15/046* (2013.01); *A61B 2018/266* (2013.01); *A61B 2090/3784* (2016.02)

(58) Field of Classification Search
CPC .................................. A61B 18/20; A61N 5/06
See application file for complete search history.

(56) References Cited

U.S. PATENT DOCUMENTS

| | | | | |
|---|---|---|---|---|
| 5,779,696 | A * | 7/1998 | Berry et al. ..................... | 606/16 |
| 6,120,516 | A * | 9/2000 | Selmon et al. ................ | 606/159 |
| 6,222,970 | B1 * | 4/2001 | Wach et al. ..................... | 385/115 |
| 7,068,867 | B2 * | 6/2006 | Adoram et al. ................. | 385/12 |

* cited by examiner

*Primary Examiner* — Lynsey Crandall

(57) ABSTRACT

A catheter and a console for a catheter. In one embodiment, the catheter includes: (1) a wall having a substantially annular cross-section and surrounding a bore, (2) a plurality of optical fibers associated with the wall and terminating at a distal end of the wall in end faces of differing, non-perpendicular orientation with respect to longitudinal axes of the plurality of optical fibers and (3) photoacoustic layers coupled to at least some of the end faces and configured to generate an ultrasonic signal in response to laser light transmitted along the plurality of optical fibers.

8 Claims, 16 Drawing Sheets

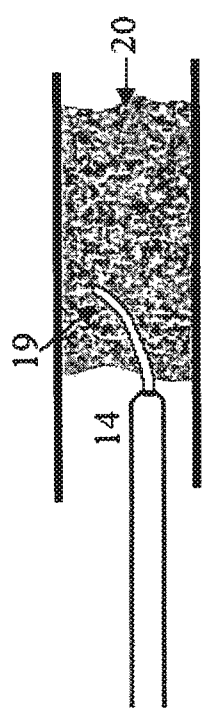
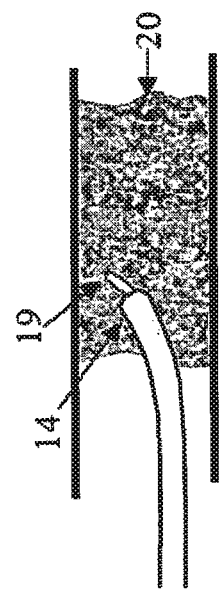
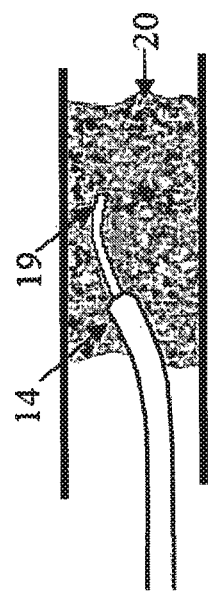
Fig. 2A
Fig. 2B
Fig. 2C

IMAGE-GUIDED LASER CATHETER

CROSS-REFERENCE TO RELATED APPLICATION

The present application claims priority based on U.S. Provisional Application Ser. No. 60/675,046, entitled "Image-Guided Laser Catheter," filed on Apr. 26, 2005, by Zhou, commonly owned with the present application and incorporated herein by reference.

TECHNICAL FIELD OF THE INVENTION

The present invention is directed, in general, to medical devices and, more specifically, to catheters and consoles for catheters used in minimally invasive procedures.

BACKGROUND OF THE INVENTION

In interventional cardiology, catheters are often inserted into a patient's artery or vein to help accomplish tasks such as angioplasty or pacemaker or defibrillator lead insertion. For example, a balloon dilation catheter expands at a site of blood vessel occlusion and compresses the plaque and improves patency of the vessel. An intravascular ultrasound catheter provides a 360° view of the lateral cross section of a vessel. Different types of atherectomy procedures are performed using devices such as the rotablade, laser catheter, or ultrasonic ablation catheter. The remarkably successful stents are deployed with the help of a balloon catheter.

Chronic total occlusion (CTO) is a disease that remains difficult to treat interventionally due to the inherent nature of the disease and the lack of adequate tools and devices. Some of the early devices, such as the Magnum™ guidewire (Schneider, Zurich, Switzerland), were made of a Teflon-coated steel shaft with an olive-shaped blunt tip. Results using this device in 800 chronic cases of CTO showed angiographic success in only 64% of the cases. One of the major failure modes was inability of the guidewire to advance.

The Kensey™ catheter (Theratech, Miami, Fla.) was a flexible polyurethane catheter with a rotating cam at the distal tip driven by an internal torsion guidewire at a speed of 10,000 rpm. Clinical evaluation in 11 patients with peripheral CTO diseases demonstrated only a 63% successful rate. The development of the device halted due to safety concerns.

The ROTACS™ low speed rotational atherectomy catheter (Oscor, Palm Harbor, Fla.) was made of several steel coils connected to a distal blunt tip of 1.9 mm. A motor drove the catheter rotation at 200 rpm. The catheter was unsuccessful due to safety concerns arising from the data that 30% of patients had extensive dissections.

The Excimer Laser Wire™ catheter (Spectranetics Colorado Springs, Colo.) comprised a bundle of silica fibers that delivered excimer laser energy to the distal tip to ablate atherosclerotic plaque. In one clinical trial, the catheter was found to have a high rate of misalignment and perforation due to a stiff guidewire tip and a lack of guidance.

The Frontrunner™ catheter (LuMend, Redwood City, Calif.) is designed with a blunt tip designed to micro-dissect its way through a CTO. A bilaterally hinged distal tip assembly is manually opened and closed by the clinician to accomplish micro-dissection. The device has found some success in treating peripheral CTOs and also has a niche in treating coronary cases with refractory in-stent CTOs wherein the stent serves to confine and guide the device through the occlusion. However, the Frontrunner™ is not suitable for the majority of coronary CTO cases due to poor steerability and the lack of guidance.

The Safe Cross™ guidewire (Intraluminal Therapeutics, Carlsbad, Calif.) combines RF ablation capability with reflectometry at the distal tip. The optical reflectometry system provides a warning signal when the guidewire tip is too close to the vessel wall, and the RF ablation provides a way to cross hard calcified plaque. The device has had some success in recent clinical trials, but it is difficult to use and has yet to show widespread acceptance by interventionalists. The issue with the Safe Cross™ guidewire is that the optical reflectometry system generates a warning signal so frequently that leaves the operator at a loss as to what to do. Such a "negative" signal only tells the clinician what to avoid, and fails to provide positive guidance for guidewire steering and advancement. Furthermore, there is no definitive indication of whether the guidewire tip is intra-luminal or extra-luminal. If for any reason the guidewire tip had accidentally perforated the vessel wall, the reflectometry signal would become useless.

Another way to provide a guidance signal for a catheter is to use laser-induced fluorescence. The healthy tissue of the artery wall and the atherosclerotic plaque attached to the wall have different fluorescent spectra or "signatures." A system that detects this fluorescent signatures should be able to tell whether the distal tip of the catheter is surrounded by healthy tissue or by plaque. A warning signal derived from laser induced fluorescence may have some advantages over the optical reflectometry signal, but the drawbacks are similar, namely, no geometric information about the diseased vessel.

A much more effective CTO intervention involves the use of imaging to guide the advancement of guidewires and catheters. Fluoroscopy is a well-established real-time external imaging modality. Fluoroscopy is used to guide many procedures, but its efficacy in CTO intervention has proven to be rather limited. Even with bi-plane projections, fluoroscopic images are hard to interpret for totally occluded vessel regions. Another issue with excessive dependence on fluoroscopy arises from the fact that CTO procedures are often time-consuming. Radiation safety as well as contrast fluid dosage are additional variables that the clinicians must monitor carefully during an already-stressful CTO intervention. Given these considerations, it is clear that an intravascular image-guided device would be highly valuable for CTO intervention.

A number of intravascular imaging devices have been developed to date. Angioscopy can supply visual information on the luminal surface, using a fiber bundle to illuminate the intraluminal space and also to collect reflected light to form an image. Angioscopy requires flushing the blood and replacing it with saline, a procedure that requires temporarily occluding the blood vessel and can cause prolonged ischemia to the heart. Because of this problem, angioscopy is used rarely other than for research purposes.

Intravascular ultrasound, or IVUS, can provide a cross-sectional image in a plane perpendicular to the catheter's axis. IVUS can image through blood with an acceptable range and has become a very successful diagnostic tool in interventional cardiology. In IVUS, an ultrasonic transducer is embedded in the distal end of an imaging catheter. The catheter is advanced through the vascular system to the target area. The transducer emits ultrasonic pulses and listens for echoes from the surrounding tissue to form a one-dimensional image. The catheter can be rotated to obtain two-dimensional imaging data, or alternatively, a solid-state IVUS with an annular array of transducers at the catheter distal surface can be used to perform 2D image scanning. Combined with a controlled pullback motion, the device can also obtain three-dimensional image data in a cylindrical volume centered on the catheter. While IVUS would at first appear to be an attractive solution for guiding the advancement of a guidewire through a CTO, existing IVUS catheters have proven difficult to advance through occluded regions having a significant degree of fibrosis. For short occlusions, a clinician might be able to use a forward-looking IVUS to guide the advancement of the guidewire through the blockage, but even such forward-looking IVUS are still under development and not yet commercially available.

Optical coherence tomography is a relatively new imaging modality that has been considered for use in CTO intervention. The module uses low-coherence light interferometry to map out the optical absorption and scattering properties of the tissue under illumination. Optical coherence tomography provides image resolution that is about 10 times better than IVUS, but the imaging range is limited to a maximum of 3 to 4 millimeters. In addition, imaging through blood is very difficult even with carefully-chosen infrared wavelength for the light source. Without a significantly better imaging range, the microscopic resolution is of little usage to CTO guidance, as the most decisive clue that the clinicians can use during a procedure is the large-scale geometric feature that reveal the contour of the blood vessel wall.

U.S. Pat. No. 4,887,605 by Angelsen, et al., describes a laser catheter with an integrated ultrasound imaging module. A housing at the distal end of the catheter contains the ultrasonic transducer. An optical fiber is placed in a central through bore and delivers laser energy to the tissue to be treated. Unfortunately, this device would be difficult to advance through a CTO, because the area that contains the ultrasonic transducer apparently lacks the ability to ablate plaque. In addition, Angelsen, et al., discloses no ability to perform forward imaging.

U.S. Pat. No. 4,587,972 by Morantte also described a combined laser ablation and ultrasound-imaging catheter. The catheter contains a fiber bundle for laser delivery and ultrasound transducers that emits in the forward direction. However, Morantte's catheter is apparently bulky and difficult to advance through CTOs.

What is needed in the art is a fundamentally new catheter not only capable of performing both tissue imaging and ablation, but also capable of being readily advanced through occluded blood vessels. What is still further needed in the art is a catheter that can be used in conjunction with conventional metal guidewires or with ablative guidewires in a procedure. What is yet further needed in the art is a catheter that is useful for percutaneous transluminal therapy of CTOs in both the coronary and peripheral systems.

SUMMARY OF THE INVENTION

To address the above-discussed deficiencies of the prior art, the present invention provides, in one aspect, a catheter. In one embodiment, the catheter includes: (1) a wall having a substantially annular cross-section and surrounding a bore, (2) a plurality of optical fibers associated with the wall and terminating at a distal end of the wall in end faces of differing, non-perpendicular orientation with respect to longitudinal axes of the plurality of optical fibers and (3) photoacoustic layers coupled to at least some of the end faces and configured to generate an ultrasonic signal in response to laser light transmitted along the plurality of optical fibers. Catheters typically have a port, located toward their proximal end, for receiving a guidewire and admitting it into the bore. Catheters also have a coupler at their proximal end to which a console is typically attachable. The wall, as that term is used herein, therefore should not be expected to have a substantially annular cross-section along the entire length of the catheter. Also, the plurality of optical fibers need not include all optical fibers associated with the wall.

In another aspect, the present invention provides a console for a catheter. In one embodiment, the console includes: (1) a coupler, (2) a first laser source configured to generate a first laser signal at a first wavelength and transmit the first laser signal to the coupler, (3) a second laser source configured to generate a second laser signal at a second wavelength and transmit the second laser signal to the coupler, (4) a third laser source configured to generate a third laser signal at a third wavelength, (5) a beam splitter coupled to the third laser source and configured to split the third laser signal into first and second beams and transmit the second beam to the coupler, (6) a photorefractive grating configured to generate an interference signal from the first beam and the second beam returned from the coupler, the interference signal indicating a phase shift between the first and second beams and (7) a processor coupled to the photorefractive grating and configured to generate an image from the interference signal.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention.

BRIEF DESCRIPTION OF THE DRAWINGS

For a more complete understanding of the invention, reference is now made to the following descriptions taken in conjunction with the accompanying drawing, in which:

FIGS. 2A, 2B and 2C together illustrate a schematic diagram of one embodiment of an image-guided laser catheter constructed according to the principles of the present invention and the manner in which a CTO may be crossed using a guidewire;

DETAILED DESCRIPTION

Figure 1:
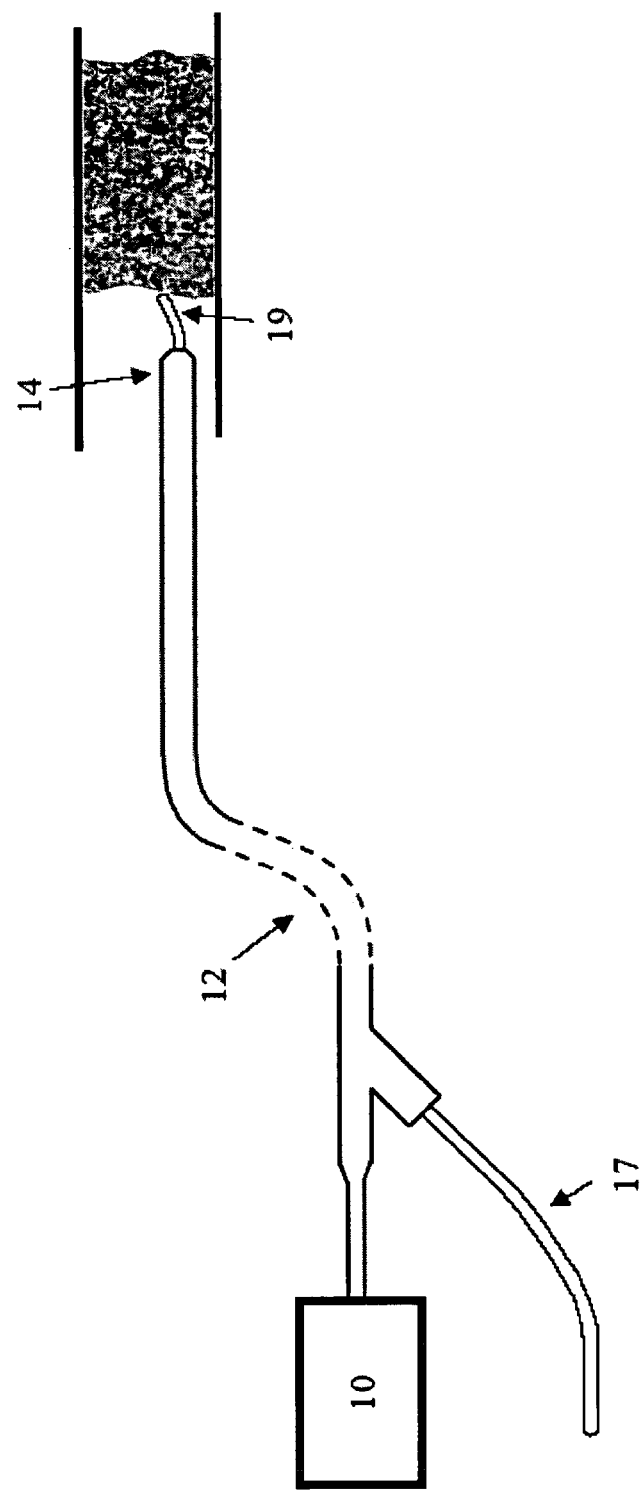
FIG. 1 illustrates a schematic diagram of one embodiment of an image-guided laser catheter constructed according to the principles of the present invention and a guidewire.

Referring initially to FIG. 1, illustrated is a schematic diagram of one embodiment of an image-guided laser catheter 12 constructed according to the principles of the present invention and a guidewire 17. FIG. 1 shows the catheter 12 as it would be used to cross a vascular stenosis. The guidewire 17 is first introduced into the patient's blood vessel percutaneously and advanced to a location proximal to an occlusion 20. A distal tip 19 of the guidewire 17 may have a slightly curved shape to allow the operator to steer the advancement direction of the guidewire 17. The catheter 12 is then introduced into the vessel over the guidewire 17. The catheter 12 has its proximal end (not separately referenced) connected to a console 10.

The catheter 12 and console 10 together provide a way to generate real-time intravascular images as well as a way to deliver ablative energy to the distal end 14. The embodiments to achieve these functions will be disclosed in detail later in this patent.

The guidewire 17 and catheter 12 can be advanced through a stenosis 20 using an iterative technique to be described now, and as illustrated in FIGS. 2A, 2B and 2C. First the catheter's distal end 14 is brought into close proximity to the guidewire's distal end 19. The intravascular imaging function of the catheter 12 is advantageously activated at this point, allowing clinicians (not shown) to visualize the position of the guidewire tip 19 relative to the vessel lumen. Under this visual guidance, the guidewire tip 19 is steered and advanced within the vessel lumen, as shown in FIG. 2A.

The amount of forward movement of the guidewire tip 19 should be small to avoid entering subintimal space or perforating the vessel wall. A tip 14 of the catheter 12 is then advanced forward over the guidewire 17, as shown in FIG. 2B. Should it become difficult to advance the catheter 12 during this step, an ablative energy can be delivered to the tip of the catheter 12 to help the advancement. Once the catheter tip 14 is brought close to the guidewire tip 19 again, the clinician can once more activate the catheter's imaging function to guide steering the guidewire tip 19 and moving it further ahead, this is illustrated in FIG. 2C. After the guidewire is advanced forward, the catheter is again advanced over-the-wire, as illustrated in FIG. 2D. The process repeats itself until the guidewire and the catheter have crossed the stenosis 20. In summary, this technique advances the guidewire 17 and the catheter 12 in an alternative pattern.

The steering and advancement of the guidewire 17 is under the visual guidance of the intravascular image provided by the catheter 12. On the other hand, the advancement of the catheter 12 is done over the guidewire 17 and is under the mechanical confinement of the guidewire 17. This mutually-guided movement of guidewire 17 and catheter 12 markedly increases the degree of safety in crossing the occlusion.

Figure 3:
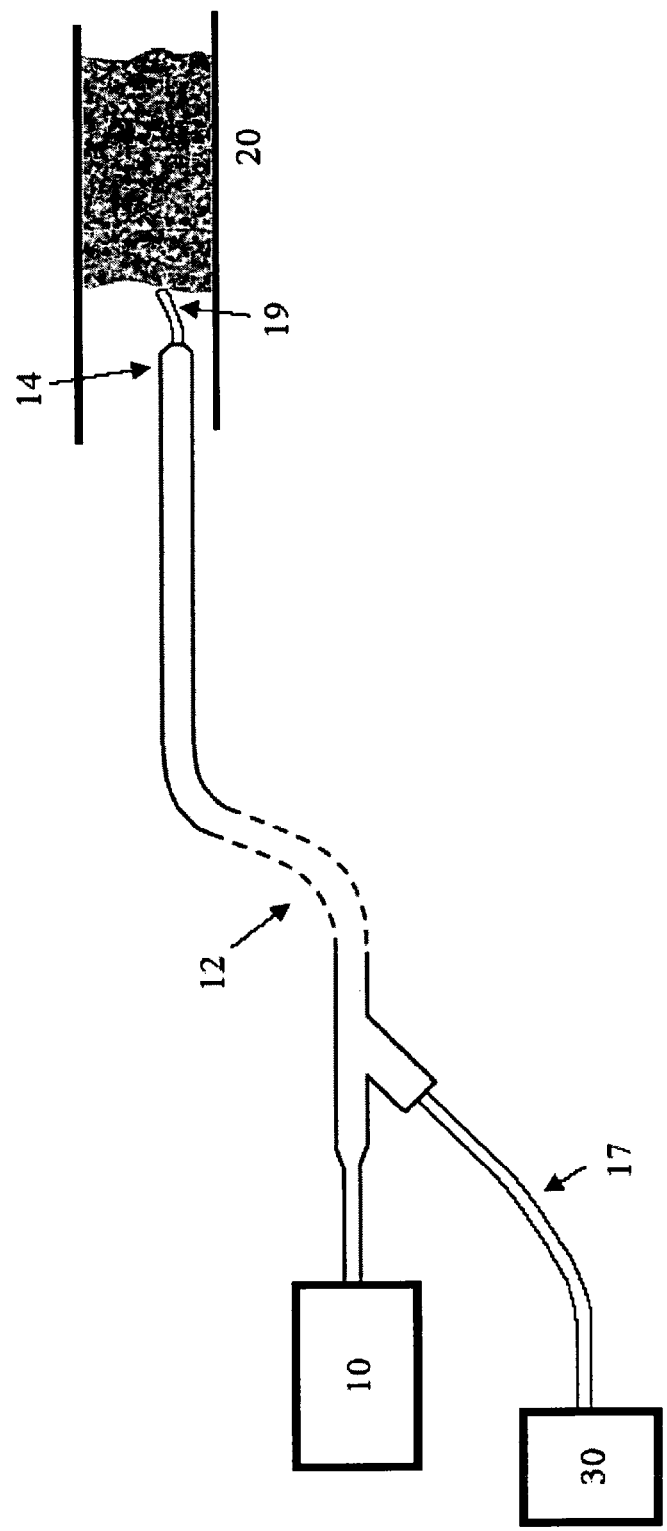
FIG. 3 illustrates a schematic diagram of an image-guided laser catheter constructed according to the principles of the present invention and the manner in which the catheter can be used with an ablative guidewire.

Turning now to FIG. 3, illustrated is an alternative embodiment of the catheter 12 in which the catheter 12 works in conjunction with a guidewire 17 having an ablative capability. The ablative capability of the guidewire 17 can be useful in cases where the stenosis to be crossed has a high degree of calcific fibrosis and is refractory to conventional guidewires. The guidewire 17 is connected to a console 30 which generates and couples the ablative energy into the guidewire 17. Some examples of such ablative guidewires that can be used are a laser guidewire (e.g., commercially available from Spectranetics), ultrasonic ablation guidewire (e.g., commercially available from the Guidant Corporation), and RF ablation guidewire (e.g., commercially available from Intraluminal Therapeutics).

Figure 4A:
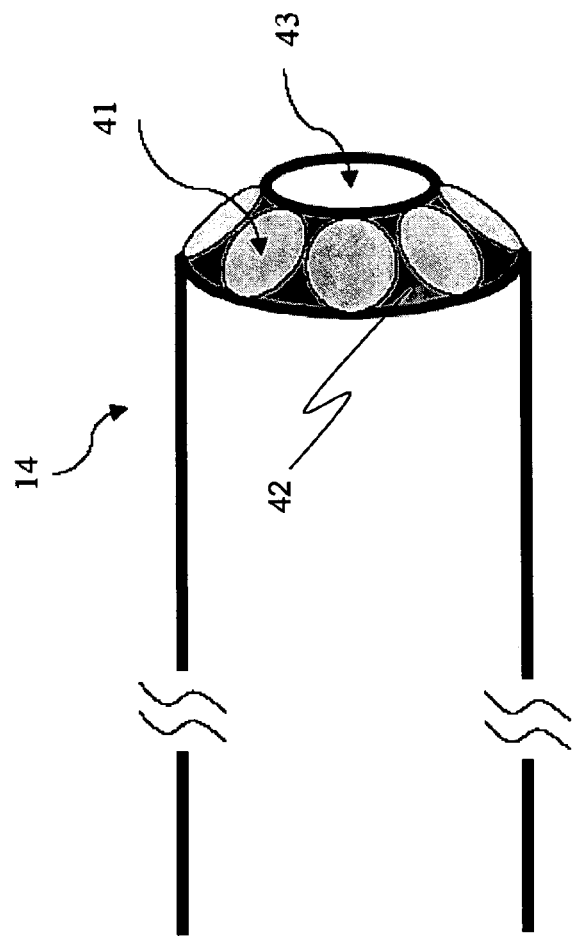
FIG. 4A illustrates an isometric view of a distal end of the catheter of FIG. 1.
Figure 4B:
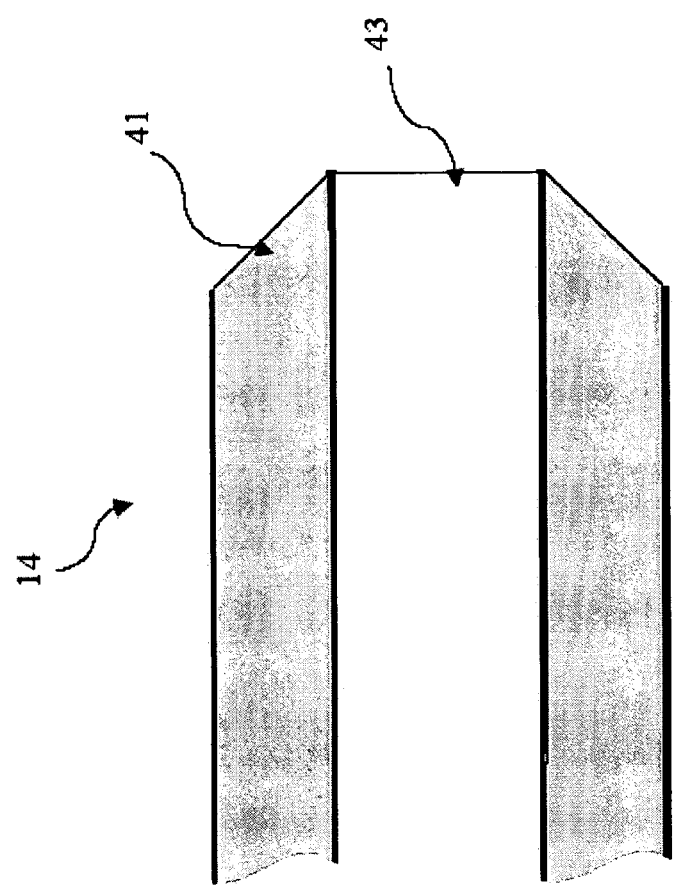
FIG. 4B illustrates a cross-sectional lateral view of the distal end of the catheter of FIG. 1.
Figure 4C:
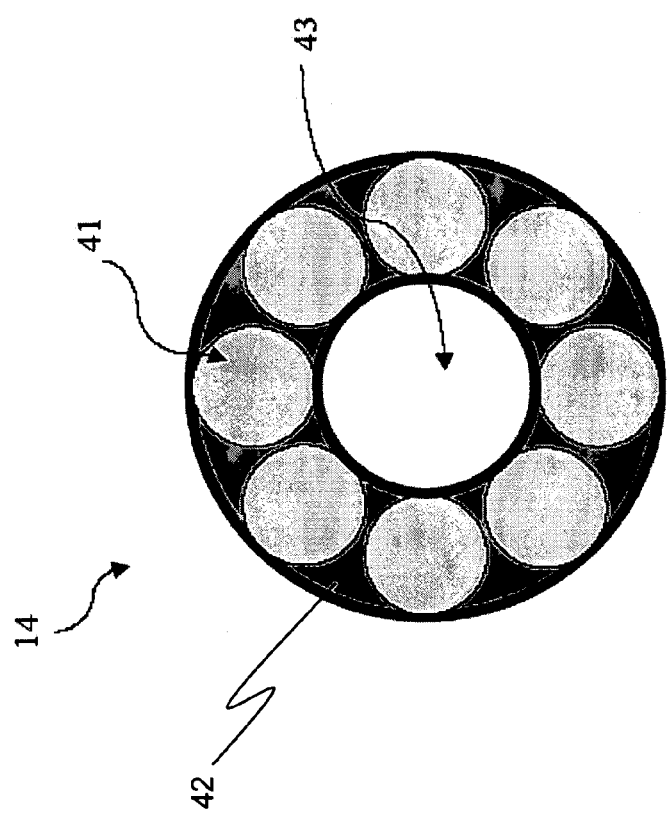
FIG. 4C illustrates another cross-sectional end view of the distal tip of the catheter of FIG. 1.

FIGS. 4A-C show the details of an example embodiment of the distal end 14 of the catheter 12. FIG. 4A is an isometric view illustrating a wall 42 having a substantially annular cross-section and an annular array of optical fibers (one of which designated 41) associated with (e.g., located in) the wall 42 and emerging at a distal end surface thereof. The annular array may contain any number of individual fibers. In one embodiment, the number of individual fibers ranges between 4 and 256 individual fibers (FIG. 4 shows eight).

A bore 43 at the center of the catheter 12 allows passage of a suitable guidewire, for example, a 0.014" guidewire. The end of an optical fiber 41 is cut and polished substantially flat at an angle substantially non-perpendicular to the fiber's longitudinal axis. In the illustrated embodiment, the annular array is assembled such that each fiber's end face has a unique orientation. The catheter's distal end 14 is approximately frustroconical, with the bore 43 at the center of the frustrocone. This is further illustrated in FIG. 4B, which is a simplified cross-sectional drawing of the catheter distal end 14. The cross-section is taken at a plane containing both the longitudinal axis of the catheter and the longitudinal axis of a fiber 41 in the annular array. FIG. 4C illustrates another cross-sectional view of the distal end 14 where the cross-sectional plane is perpendicular to the catheter's longitudinal axis.

Figure 5A:
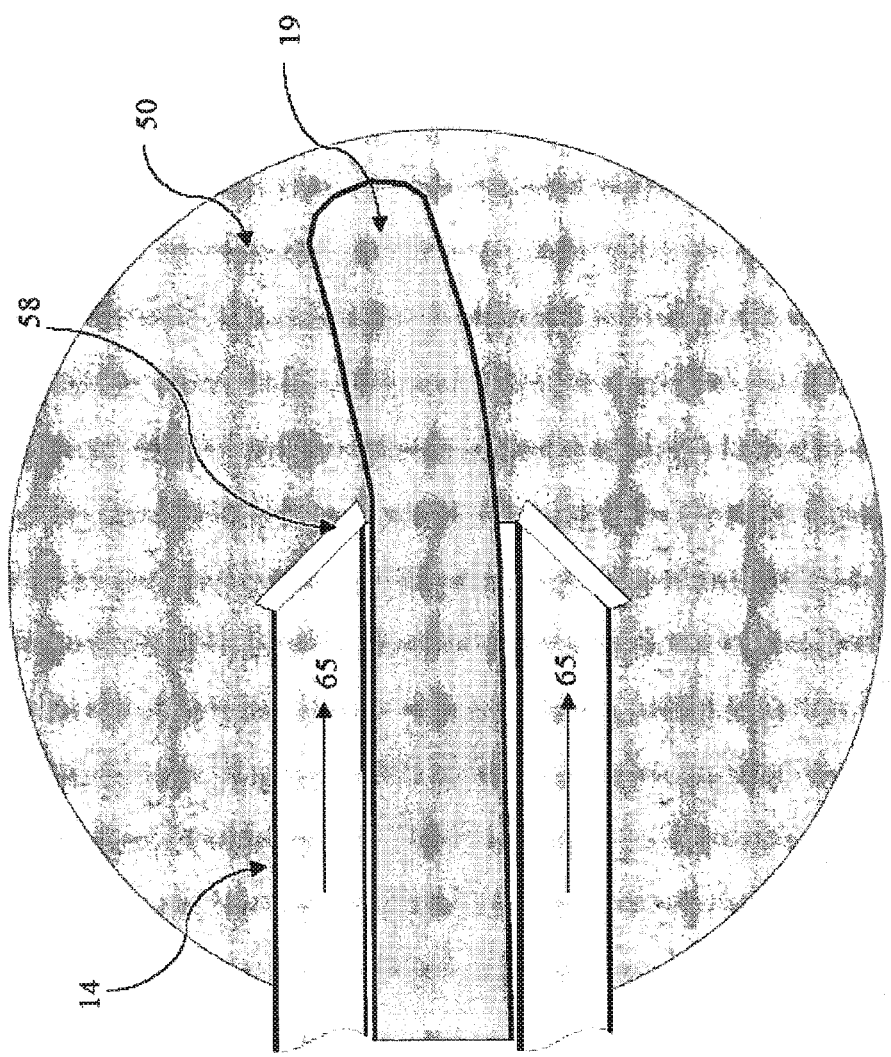
FIG. 5A illustrates an isometric view of the distal end of the catheter of FIG. 1 and guidewire showing, in particular, a laser ablation region.
Figure 5B:
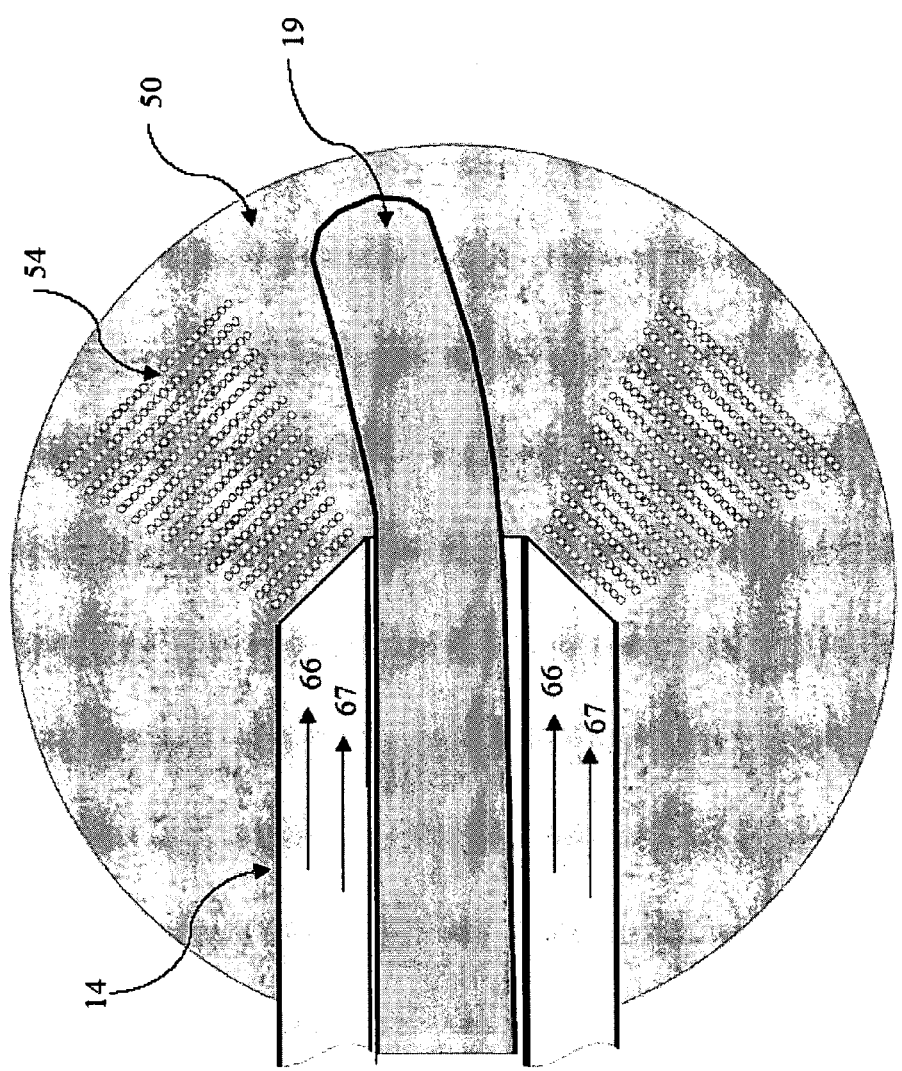
FIG. 5B illustrates an isometric view of the distal end of the catheter and guidewire showing, in particular, laser-assisted ultrasonic imaging.

The catheter 12 can operate in two distinct modes: ablation mode and imaging mode. FIG. 5A-B illustrate some qualitative features of the two modes. The catheter's distal tip 14 is shown in a cross-sectional view with the guidewire tip 19 and a surrounding medium 50 (which could be either healthy tissue, plaque, blood or a combination of them, depending on location). FIG. 5A illustrates the ablation mode. In this mode, ablative laser energy 65 is coupled into the fibers at the proximal end of the catheter 12 and exits the distal end of the fiber array to ablate the surrounding tissue.

The ablative laser energy 65 can be coupled into the catheter 12 using either a sequential or a parallel approach. With the sequential approach the ablative laser energy 65 is coupled into one fiber at a given time. The fibers in the annular array shown in FIG. 4A are selected one by one sequentially to receive ablative energy coupling. When averaged over a period of time, each fiber in the annular array should have delivered an equal amount of ablative laser energy 65; however, this need not be the case. With the parallel approach, the ablative laser energy 65 is split at the input end and is coupled into all fibers simultaneously.

The choice of the energy coupling approach may affect things such as energy efficiency and ablation speed. A number of pulsed lasers are suitable for tissue ablation, examples range from the excimer lasers in the ultraviolet region to various solid state lasers in the near infrared to carbon dioxide laser at 10.6 microns wavelength. A particularly effective ablative energy is the 308 nm UV pulse from a XeCl excimer laser. In the case of the 308 nm laser, the energy is typically absorbed by a thin layer 58 immediately adjacent to the end face of the fibers in the catheter 12, as is illustrated in FIG. 5A.

A second mode that the catheter 12 can operate at is the imaging mode, and FIG. 5B illustrates some features of this mode. In this mode, a second laser 66 and a third laser 67 are transmitted by the fibers in the catheter 12 and they generate acoustic wave 54 and detect acoustic echo from objects in the medium. Similar to the ablation mode, the lasers 66 and 67 can be coupled into the fiber using either a sequential approach or a parallel approach.

Figure 6C:
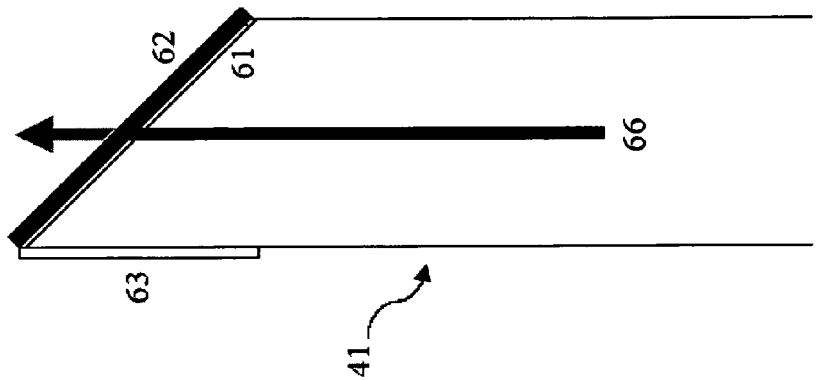
FIGS. 6A, 6B and 6C together illustrate further details of the optical fiber at the distal tip of the catheter of FIG. 1.
Figure 6B:
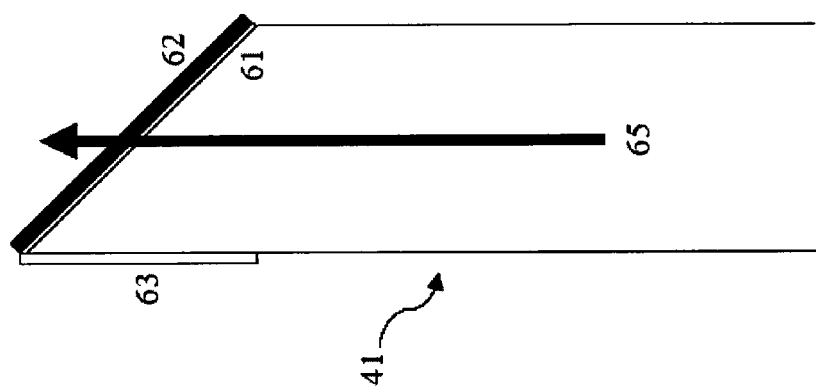
Figure 6A:
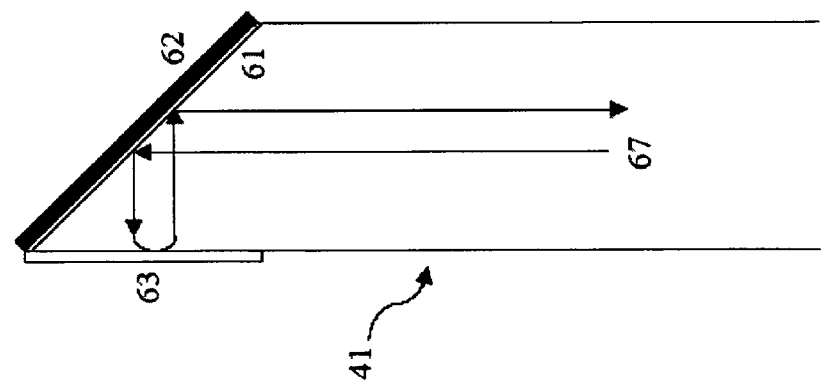

FIGS. 6A, 6B and 6C show further details of the construction of the optical fibers in the catheter 12. An optical fiber 41 in the catheter 12 has an angle-polished end face. A layer of optical coating 61 is deposited on the end face. A thin photoacoustic layer 62, which could also be called a "filter plate," is bonded on top of the coating 61. A reflective coating 63 is deposited on one side of the fiber as shown.

The fiber 41 is configured to transmit three types of laser light. The first laser 65 provides the ablation energy, an example of which is a pulsed 308 nm excimer laser. The second laser 66 generates the acoustic excitation, an example of which is a 1.06 micron pulsed Neodymium-doped Yttrium Aluminum Garnet, or Nd:YAG, laser. Another example is a 532 nm, frequency-doubled, pulsed YAG laser. The third laser 67 detects the acoustic echo reflected from an object near the catheter tip 14, an example of which is the continuous-wave 532 nm frequency-doubled YAG laser. The coating 61 is dichroic, meaning that it reflects substantially all of the energy from the third laser 67, but transmits substantially both the energy from the first laser 65 and the energy from the second laser 66. The coating 63 is a high reflector that reflects substantially all the energy of the third laser 67. FIG. 6A illustrates that the energy from the third laser 67 traveling in the fiber 41 is reflected twice by the coating 61 and once by coating 63 and returns toward the input end of the fiber.

FIG. 6B illustrates that the ablation laser 65 transmits through both the coating 61 and the photoacoustic layer 62 and exits into the surrounding medium. FIG. 6C illustrates that the acoustic excitation laser 66 transmits through the coating 61 and is then absorbed significantly by the photoacoustic layer 62. The dichroic coating 61 and the high-reflector coating 63 can be designed by standard optical coating software and implemented with a highly-reliable and well-known process such as ion-beam sputtering. The photoacoustic layer 62 can be made from a wavelength-selective absorptive glass such as the color glass filter from, e.g., Schott Inc. An example would be the UG11 glass which is highly transparent at 308 nm but highly absorptive at both 1.06 micron and 532 nm wavelengths. The energy from the excitation laser 66 is significantly absorbed by the photoacoustic layer 62 and generates an acoustic pulse via the photoacoustic effect. The duration and strength of the acoustic pulse generated is determined by the duration and intensity of the second laser 66. For example, if the energy from the second laser 66 has a pulsewidth of 100 nanoseconds, then the acoustic pulse will also have a duration of approximately 100 nsec, and the ultrasonic bandwidth will be approximately 10 MHz. Such an ultrasonic wave can propagate quite far (for example, 10 mm) in tissue or in blood without suffering excessive attenuation.

Figure 7:
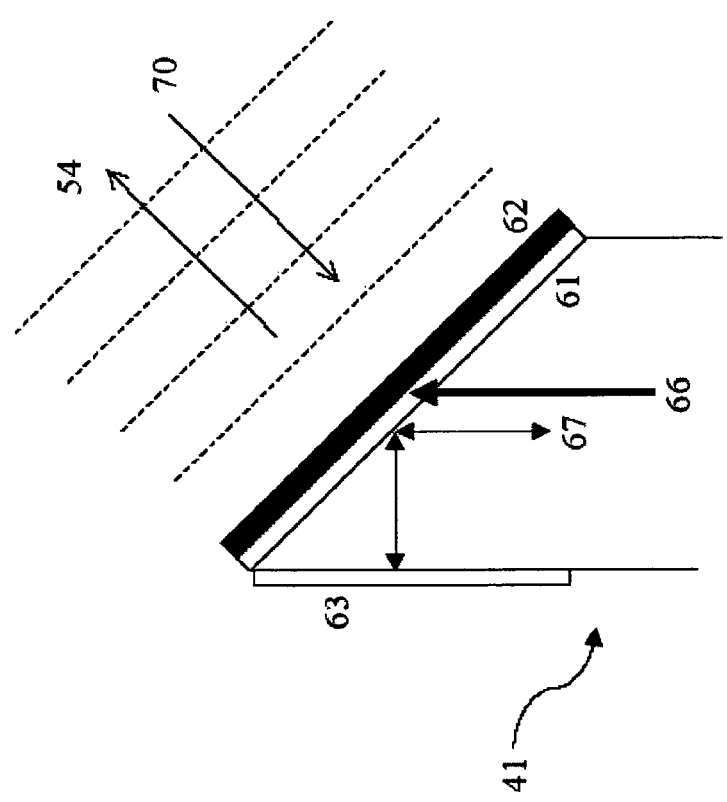
FIG. 7 illustrates a magnified view of the distal tip of a fiber of the catheter of FIG. 1 showing, in particular, ultrasound generation at the distal tip of the fiber.

FIG. 7 further illustrates elements involved in acoustic pulse excitation and detection at the distal tip of a fiber 41. The energy from the excitation laser 66 is absorbed by the photoacoustic layer 62. The absorbed energy causes a rapid rise in temperature of the photoacoustic layer 62. The photoacoustic layer 62 expands under thermal stress and causes a rapid pressure change at its surface. The pressure change is transmitted into the surrounding medium and propagates away from the photoacoustic layer 62 in the form of an ultrasonic acoustic wave 54. The pulsewidth and intensity of the energy from the excitation laser 66 largely determines the acoustic wave frequency and amplitude, although the acoustic impedance of the photoacoustic layer 62 itself and the surrounding medium should also be taken into account. Objects in the surrounding medium will reflect the outgoing acoustic wave 54 according to their acoustic impedances and generate an acoustic echo signal 70 that propagates back toward the end face of the fiber 41. The acoustic echo pressure can provide useful information about material type and property. At a given moment in time, the acoustic echo pressure is directly related to the mechanical properties of an object in the field at a given distance away. The echo signal over time provides one-dimensional range data of the object along the longitudinal direction (the direction of ultrasound propagation). The arrival time of an echo determines the longitudinal position of a reflector, and the corresponding acoustic echo pressure determines the acoustic impedance of that reflector. The detection of acoustic echo is facilitated by having a detection laser 67 that co-propagates with the excitation laser 66 in a fiber. The detection laser 67 is reflected twice by coating 61 and once by coating 63 so that it back-propagates toward the input end of the fiber 41. The acoustic echo 70 travels through the photoacoustic layer 62 and perturbs the coating 61. The perturbation on the coating 61 caused by the acoustic echo 70 generates a corresponding optical phase shift on the reflected light 67. The amount of phase shift imposed on light 67 is proportional to the acoustic pressure present at the coating 61. This optical phase shift can be detected using a technique to be further disclosed later in FIG. 12. Therefore, not only the presence, but also the magnitude of the acoustic signal of the echo 70 can be detected.

According to this mechanism, a fiber 41 can act as a one-dimensional imaging device. As illustrated in FIG. 4A, each fiber in the catheter 12 has its end face pointing at a unique normal direction. Therefore the annular ring of fibers in the catheter 12 can perform two-dimensional ultrasonic imaging in the forward direction. The imaging space would be the two-dimensional frustrocone formed by the surface normals of all the fibers in the annular array. The image obtained would be qualitatively similar to that from the forward-looking IVUS.

Thus the annular array of fibers in the catheter 12 serve the dual purpose of carrying ablative energy in the ablation mode, and generating acoustic waves and detecting acoustic images in the imaging mode. As pointed out in the Background of the Invention section above, a technique to integrate both functionalities over the same catheter is novel and highly desirable.

Figure 8:
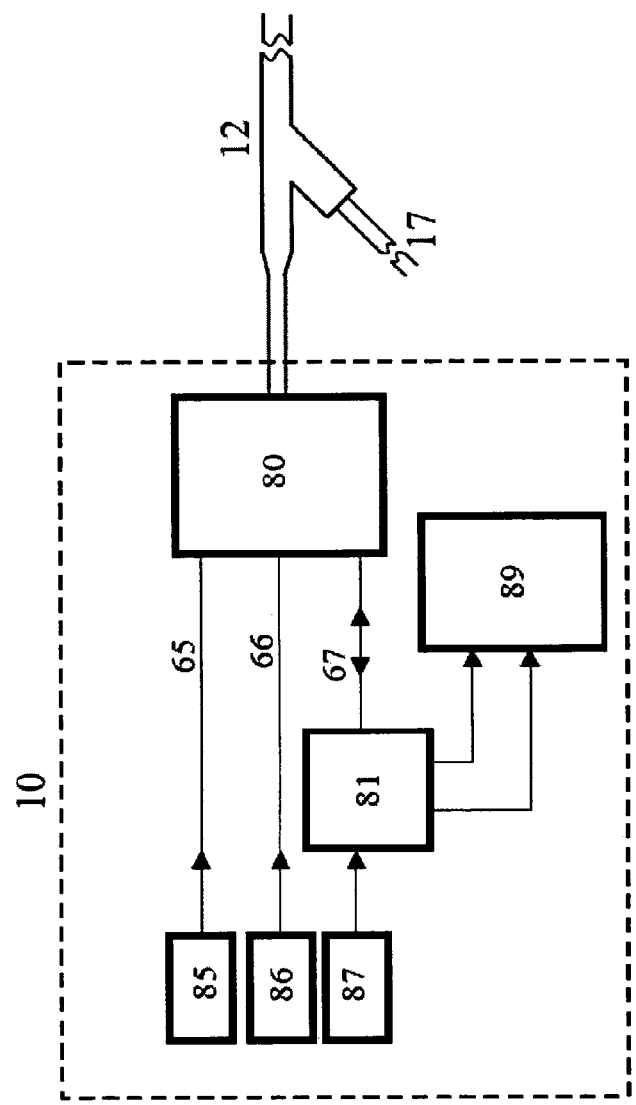
FIG. 8 illustrates a block diagram of one embodiment of a console associated with the catheter of FIG. 1 and constructed according to the principles of the present invention.

Turning now to FIG. 8, a way of coupling laser energy into the catheter 12 and a way of detecting phase changes experienced by the detection laser 67 will be described. As illustrated by FIG. 8, a console 10 couples lasers 65, 66, and 67 into the catheter 12, as well as receiving and processing the reflected detection laser light 67. The ablation laser 85 generates the ablation laser light 65, the acoustic excitation laser 86 generates the excitation light 66, and the detection laser 87 generates detection light 67. When the catheter 12 operates in ablation mode, the lasers 86 and 87 are off, while laser 85 is on. When the catheter 12 operates in imaging mode, the lasers 86 and 87 are on, while laser 85 is turned off. Laser 85 and 86 are directly sent to a coupler 80, whereas laser 87 first passes through a beam splitting module 81 before being sent to the coupler 80. The beam splitting module 81 allows part of the laser energy 87 (a second beam) to pass through while splitting the rest of the laser energy (a first beam) toward a processing module 89. The detection light 67 reflected from the distal end of catheter 12 is also routed by the unit 81 toward the processing module 89, which extracts the phase change information on light 67 caused by an acoustic echo.

Figure 9:
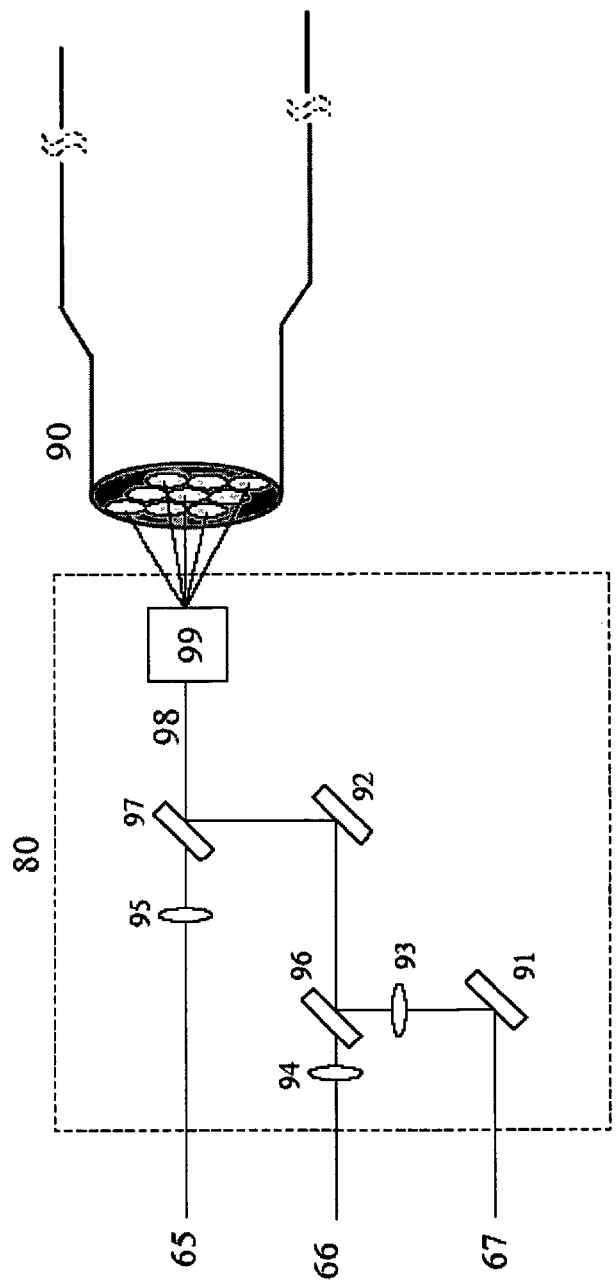
FIG. 9 illustrates a first alternative embodiment of a coupler in the console of FIG. 8.
Figure 10:
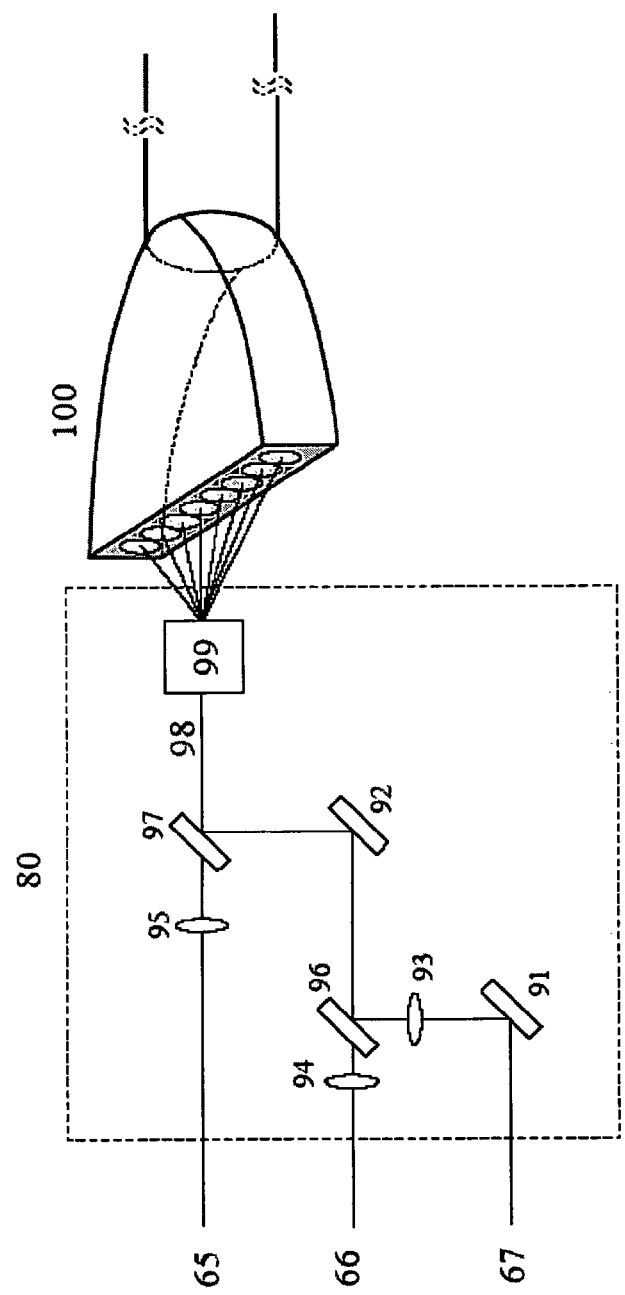
FIG. 10 illustrates a second alternative embodiment of the coupler in the console of FIG. 8.
Figure 11:
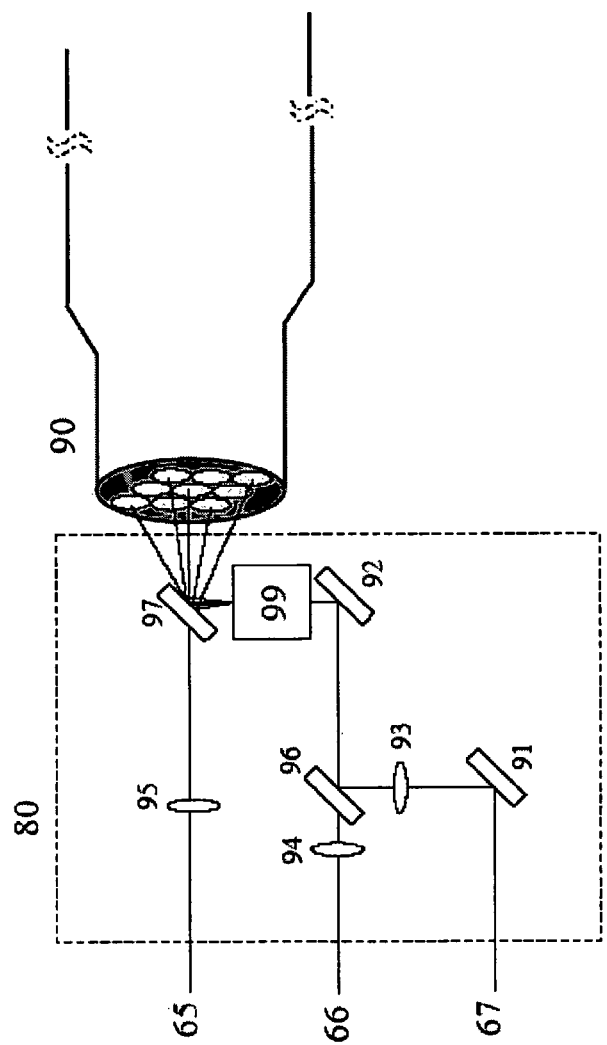
FIG. 11 illustrates a third alternative embodiment of the coupler in the console of FIG. 8.

FIGS. 9, 10 and 11 illustrate three alternative embodiments of the coupler 80. FIG. 9 shows that the three laser light sources 65, 66, 67 are combined into a single beam 98 using mirrors 91, 92, lenses 93, 94, 95, and wavelength multiplexers 96, 97. The multiplexers 96 and 97 can be standard dichroic filters that selectively reflect and transmit light according to the wavelength. A laser beam scanner 99 can be used to direct the beam 98 into each fiber sequentially. Note that the size of the proximal end 90 of the catheter 12 is highly exaggerated in the drawing for viewing clarity. The fibers at the proximal end need not be maintained to form the same annular ring pattern as the distal end 14. It can be bundled together as shown in FIG. 9, or it can be spread out to form a linear array, as shown in FIG. 10. One of the advantages of a linearized proximal end 100 of the catheter 12 may be that it helps simplify the design of the beam scanner 99 since it requires only a one-dimensional scan. Other techniques to arrange the proximal end fibers are also possible but need not be enumerated here. FIG. 11 shows a slightly different configuration for the coupler 80. The difference here is that only the excitation laser 66 and detection laser 67 are combined and sent to a beam scanner 99. The beam scanner sequentially directs this combined beam into the fibers at the catheter 12 proximal end 90. On the other hand, the ablation laser 65 is properly expanded and coupled into the fibers using the parallel approach, meaning the energy is simultaneously directed to all the fibers in the catheter 12 proximal end 90.

Figure 12:
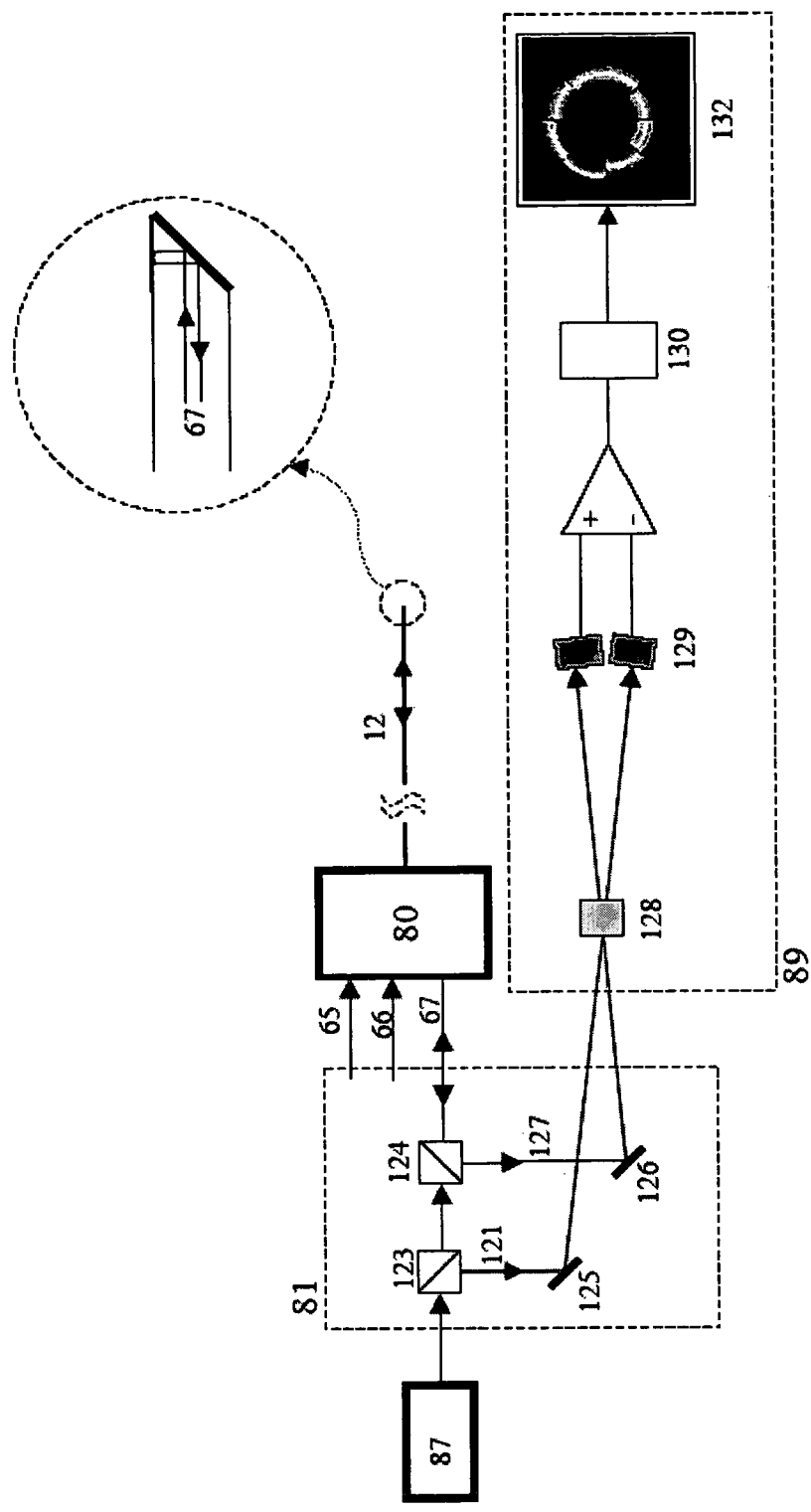
FIG. 12 illustrates a block diagram of one embodiment of an acoustic echo detection module configured to detect and process an acoustic echo signal to generate an image.

FIG. 12 illustrates an example embodiment of the beam splitting module 81 and the processing module 89 that were shown in FIG. 8. The output from laser 87 is split by beam splitters 123, 124 into light beams 67, 121. The detection light 67 is reflected from the distal end of catheter 12, back-propagates through the system, and is routed by splitter 124 into an orthogonal direction as laser beam 127. Light beams 121, 127 are reflected by mirrors 125, 126 respectively toward a beam-combiner, taking the form of a photorefractive crystal 128 in the illustrated embodiment, where they intersect and interfere with each other. Although a more conventional beam-combiner such as a laser beam-splitter can be used, a photorefractive crystal has some advantages. A DC high voltage (not shown in FIG. 12) can be optionally applied across the crystal in some cases. A pair of identical photodetectors 129 receives the transmitted intensity of the light beams, and the difference in the detector outputs are amplified by a differential amplifier. The pair of matched detectors followed by a differential amplifier is often referred to, together, as a balanced detector. A computer or other data acquisition device 130 can be used store the received data. Acoustic echo data from different fibers in the catheter 12 can be collected and the corresponding two-dimensional data can be displayed as a gray-level image on, e.g., a display 132.

The photorefractive crystal 128 can produce a space-charge field according to the interference fringe pattern formed by light beams 121, 127. The linear electro-optic effect (or the Pockle's Effect) is the effect where the refractive index of a material is changed by an amount proportional to the applied electric field. The space-charge field in the photorefractive crystal 128, in conjunction with the linear electro-optic effect, produces a three-dimensional index grating, known as a photorefractive grating. The light beams 121, 127 diffract off of this grating and into each other's direction coherently, therefore the total optical power seen by either one of the detectors 129 is sensitive to the relative optical phase between light beams 121, 127. Specifically, Equation (1), below, approximately describes the relationship:

$$I_{SIG}^A = I_0 + I_1 \cos(\phi_G + \phi_{US}) \quad (1)$$

where $I_{SIG}^A$ is the optical power received at one of the photodetectors, $I_0$ is a constant determined by the respective powers of the interfering beams 121, 127, and $I_1$ is a constant determined jointly by the respective powers of the interfering beams 121, 127, by the coherence length of the laser source 87, and by the photorefractive grating in the crystal 128. The phase bias $\phi_G$ is the phase-shift between the photorefractive grating and the interference fringe formed by the intersecting light beams 121, 127. The ultrasonic echo pressure modulates the optical phase of light 127, and the corresponding phase shift $\phi_{US}$ is a quantity that changes rapidly with time.

The signal $I_{SIG}^B$ detected by the other detector of the pair 129 can be approximately expressed as (for simplicity of the discussion, the beams 121, 127 will be assumed to have equal intensities):

$$I_{SIG}^B = I_0 - I_1 \cos(\phi_G + \phi_{US}) \quad (2)$$

The difference between the two detector outputs is thus proportional to $\cos(\phi_G + \phi_{US})$.

Since the grating phase shift is approximately a constant for a given type of crystal, information about the ultrasound-induced phase shift $\phi_{US}$ can be deduced from the output signal of the differential amplifier. In turn, the ultrasonic echo pressure at the distal end of catheter can be obtained.

The order of events during ultrasonic echo detection by this interferometer of FIG. 12 is as follows. The photorefractive grating in the crystal 128 is first formed by the light beams 121, 127, reaching full strength in typically 1 to 1000 milliseconds. At this point in time the system is at steady state and the signal from the detector 129 is constant and will remain so until ultrasonic waves are generated. A laser pulse 66 is then launched into a fiber in the catheter 12. This laser pulse generates an ultrasonic wave in the medium surrounding the distal end of the catheter 12. The ultrasonic echo returns to the distal end of the catheter 12 within a short time, typically from 1 to 10 microseconds, immediately following the excitation laser pulse. During this short period of time, the optical phase of reflected light 67, and hence the light beam 127, is modulated by the ultrasonic echo. The photorefractive grating in the crystal 128 remains significantly unchanged during this time. The photorefractive grating combines the light beams 121, 127, causing them to interfere with each other. The signal from the detector 129 indicates rapid changes corresponding to the ultrasonic echo. After the ultrasonic echo is detected, the system goes back to its steady state, with the laser 66 being off, the laser 67 remaining on and the photorefractive grating in crystal 128 being at full strength. If further ultrasonic echo data are needed, the process can repeat itself and start again by launching a laser pulse 66 into the catheter 12. The time between successive excitation laser pulses 66 is typically a fraction of a millisecond or longer. The physics of the photorefractive effect is complex but well documented and well understood to those skilled in the pertinent art, so it will not be explained here in any more detail.

Crystals suitable for the application here include, but not limited to, the following: Barium Titanate ($BaTiO_3$), Lithium Niobate ($LiNbO_3$), Potassium Niobate ($KNbO_3$), Bismuth Silicate ($Bi_{12}SiO_{20}$ or BSO), Bismuth Titanate (BTO) and Gallium Phosphate (GaP).

The use of a crystal such as BSO is further advantageous in that it has a fast response time, typically from 1 millisecond to 100 milliseconds, therefore it can adaptively track any slow drifts in the interferometer while allowing fast, Mega Hertz range ultrasonic signals to be detected. In addition, the photorefractive grating formed in a BSO crystal under an externally-applied electric field has a phase shift relative to the interference fringe that causes the phase bias $\phi_G$ in Equations (1) and (2) to be approximately $\pi/2$ radiant. This particular phase bias is advantageous because it makes the detected signal $I_{SIG}$ to be highly sensitive to small changes in the ultrasound-induced phase shift $\phi_{US}$. In other words, the interferometer is automatically maintained at an optimum phase bias point, which provides high sensitivity for ultrasonic signal detection.

Figure 13:
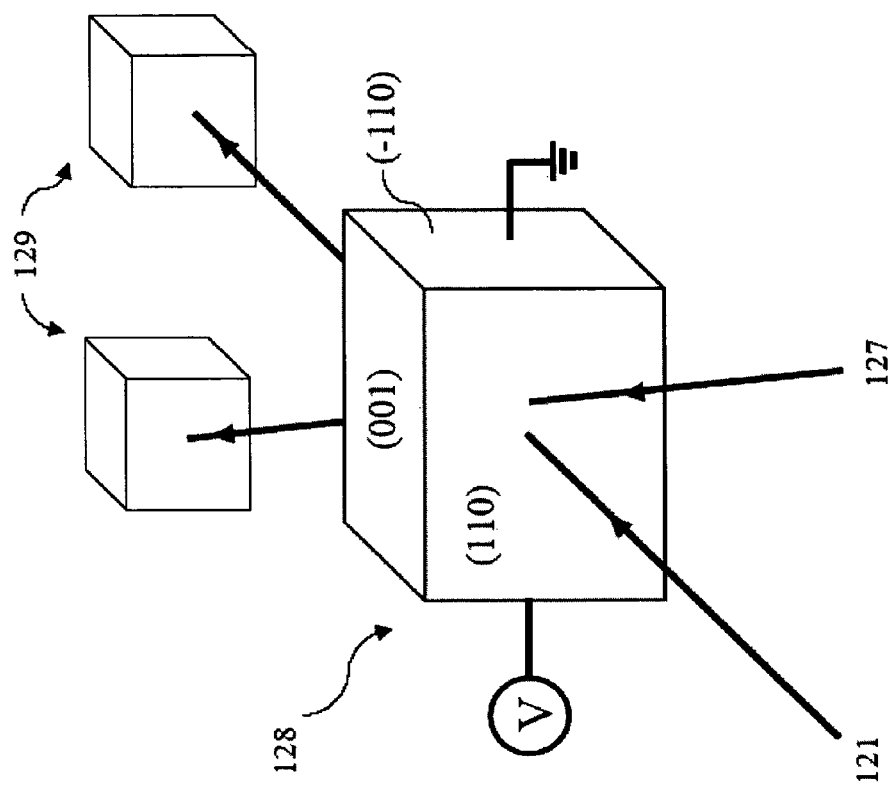
FIG. 13 illustrates one embodiment of a photorefractive crystal used in the acoustic echo detection module of FIG. 12.

One particular way to use a $Bi_{12}SiO_{20}$ crystal for this application is further illustrated in FIG. 13. The crystal is cut and polished along the <001> and <110> directions, so that the crystallographic planes are as shown. The size of the crystal is typically in the range of 1 to 10 millimeters for each dimension. Electrodes can be deposited onto the (−110) planes and a DC electric field (typically in the range of 1 to 10 KV/cm) is applied across the material. The DC electric field allows the recording of photorefractive grating with the optimum phase shift relative to the interference fringe. In addition, the applied field improves the strength of the photorefractive grating and hence also positively impact detection sensitivity. The photorefractive grating vector here is generally perpendicular to the <001> axis of the crystal.

Although the present invention has been described in detail, those skilled in the art should understand that they can make various changes, substitutions and alterations herein without departing from the spirit and scope of the invention in its broadest form.

What is claimed is:

1. A catheter, comprising:
    a wall having a substantially annular cross-section and surrounding a bore; and
    a plurality of optical fibers associated with said wall, wherein each optical fiber of said plurality of optical fibers terminates at a distal end of said wall in an end face of differing, non-perpendicular orientation with respect to longitudinal axes of said plurality of optical fibers;
    wherein at least one optical fiber of said plurality of optical fibers includes:
        a reflective coating on a side proximate a distal end of said at least one optical fiber;
        a photoacoustic layer coupled to said end face and configured to generate an ultrasonic signal in response to laser light transmitted along said plurality of optical fibers; and
        a dichroic optical coating proximate said end face, said reflective coating and dichroic optical coating configured to cooperate to provide a back-propagation path away from said distal end of said at least one optical fiber.

2. The catheter as recited in claim 1 wherein said plurality of optical fibers are located in said wall.

3. The catheter as recited in claim 1 wherein said end of said wall is convex.

4. The catheter as recited in claim 1 wherein said end of said wall is substantially frustroconical and said photoacoustic layers are substantially flush with said end.

5. The catheter as recited in claim 1 wherein said end face is oriented at about 45° with respect to said longitudinal axes.

6. The catheter as recited in claim 1 wherein some of said plurality of optical fibers are free of said photoacoustic layers.

7. The catheter as recited in claim 1 wherein a proximal end of said wall is configured to terminate in a coupler associated with a console.

8. The catheter as recited in claim 1 further comprising a guidewire located in said bore.

* * * * *